US011517903B2

(12) United States Patent
Silver (10) Patent No.: US 11,517,903 B2
(45) Date of Patent: Dec. 6, 2022

(54) BIOLOGICAL AGENT SPECIMEN COLLECTION AND GROWTH SYSTEM

(71) Applicant: SYRACUSE UNIVERSITY, Syracuse, NY (US)

(72) Inventor: Robert B. Silver, Syracuse, NY (US)

(*) Notice: Subject to any disclaimer, the term of this patent is extended or adjusted under 35 U.S.C. 154(b) by 482 days.

(21) Appl. No.: 16/613,987

(22) PCT Filed: May 3, 2018

(86) PCT No.: PCT/US2018/030783
§ 371 (c)(1),
(2) Date: Nov. 15, 2019

(87) PCT Pub. No.: WO2018/204573
PCT Pub. Date: Nov. 8, 2018

(65) Prior Publication Data
US 2021/0331155 A1 Oct. 28, 2021

Related U.S. Application Data

(60) Provisional application No. 62/502,062, filed on May 5, 2017.

(51) Int. Cl.
*B01L 3/00* (2006.01)
*B01L 7/00* (2006.01)

(52) U.S. Cl.
CPC .............. *B01L 3/5029* (2013.01); *B01L 7/00* (2013.01); *B01L 2200/025* (2013.01);
(Continued)

(58) Field of Classification Search
CPC .......... B01L 5/50; B01L 5/502; B01L 5/5029; B01L 2300/06; B01L 2300/0854;
(Continued)

(56) References Cited

U.S. PATENT DOCUMENTS 5,084,245 A * 1/1992 Berke .............. G01N 33/54366
422/430
5,415,994 A * 5/1995 Imrich ................. G01N 33/569
435/5
(Continued)

FOREIGN PATENT DOCUMENTS

WO 2016131851 A1 8/2016

OTHER PUBLICATIONS

International Search Report and Written Opinion Form PCT/ISA/210 and PCT/ISA/237, International Application No. PCT/US18/30783, pp. 1-5, International Filing Date May 3, 2018, dated Jul. 13, 2018.

(Continued)

*Primary Examiner* — Jill A Warden
*Assistant Examiner* — Dwayne K Handy
(74) *Attorney, Agent, or Firm* — David Nocilly (57) ABSTRACT

A system for collecting, growing, and analyzing biological specimens that may present a health threat. The system includes separate modules for specimen collection, sample isolation, and sample analysis that can be interconnected to safety process, culture, and analyze and unknown specimen. A decapitation module allows a user to safely collect a swab tip containing an unknown sample and transport the sample to a culture module where the sample can be washed from the swab tip and isolated in a cuvette for growth and analysis. The culture module may be coupled to a base station that can provide mixing, heating and cooling, as well as optical and spectral analysis.

14 Claims, 9 Drawing Sheets

(52) U.S. Cl.
CPC . *B01L 2200/141* (2013.01); *B01L 2300/0681* (2013.01); *B01L 2300/087* (2013.01); *B01L 2300/1822* (2013.01); *B01L 2400/065* (2013.01); *B01L 2400/0644* (2013.01)

(58) Field of Classification Search
CPC ....... B01L 2300/0858; B01L 2300/087; B01L 2400/065; C12M 1/26; C12M 1/28; C12M 1/30
See application file for complete search history.

(56) References Cited

U.S. PATENT DOCUMENTS

| | | | |
|---|---|---|---|
| 9,517,467 B1 | 12/2016 | Carrano et al. | |
| 2002/0173047 A1* | 11/2002 | Hudak | B01L 3/5023 436/178 |
| 2005/0084842 A1 | 4/2005 | O'Connor | |
| 2005/0180882 A1* | 8/2005 | Tung | A61B 10/0045 422/504 |
| 2006/0094028 A1* | 5/2006 | Danna | G01N 33/56944 435/5 |
| 2010/0274155 A1 | 10/2010 | Battrell et al. | |
| 2012/0282616 A1* | 11/2012 | Zeijlstra | B01L 3/50 435/6.12 |
| 2015/0241319 A1* | 8/2015 | Chiesl | B01L 3/502761 435/7.1 |

OTHER PUBLICATIONS

International Preliminary Report on Patentability for International Application PCT/US2018/030783, filed May 3, 2018. IPRP dated Jun. 27, 2018, pp. 1-4.

* cited by examiner

FIG. 9

BIOLOGICAL AGENT SPECIMEN COLLECTION AND GROWTH SYSTEM

CROSS-REFERENCE TO RELATED APPLICATION

The present application claims priority to U.S. Provisional Application No. 62/502,062, filed on May 5, 2017.

STATEMENT REGARDING FEDERALLY SPONSORED RESEARCH OR DEVELOPMENT

This invention was made with government support under Contract Number HDTRA1-14-D-0002 awarded by the Defense Threat Reduction Agency. The government has certain rights in the invention.

BACKGROUND OF THE INVENTION

1. Field of the Invention

The present invention relates to specimen collection systems and, more specifically, to a system that can be used for the safe collection, preparation, and transportation of unknown biological agents in the field for subsequence study and analysis to include identification of biological agent or agents present in the sample.

2. Description of the Related Art

Biological threats represent a significant concern worldwide and are often encountered by agents operating remotely from the sophisticated labs and equipment that are necessary for the proper identification of the specific nature of the biological threat. In addition to being difficult to safely collect, the assessment of biological specimens requires individuals with specialized training and equipment. Thus, there is a need in the art for an effective means of safe collection and expansion of biological agents and other materials amenable to subsequent detailed analysis that can be used by non-technical operators acting in overt and covert manners.

BRIEF SUMMARY OF THE INVENTION

The present invention provides for the safe collection of biological specimens using a specimen collection system that includes a swab decapitation unit with a swab port dimensioned to accept a sample swab, a cutting instrument positioned at an end of the swab port and moveable to sever a tip of the swab, a swab receptacle for retaining the severed tip of the swab, and a valve controlled by a first interlock in communication with the receptacle. The specimen collection system also includes a growth chamber having an entry port with a second interlock that is adapted to be coupled to the first interlock and open the valve of the decapitation unit so that the entry port is in communication with the swab receptacle. The growth chamber further includes a wash receptacle positioned in the growth chamber in communication with the entry port and having a first slide that is moveable between a first position, wherein the entry port and the wash receptacle are in open communication, and a second position, wherein the entry port and the wash receptacle are isolated from each other. The growth chamber also includes a specimen receptacle coupled to the wash receptacle and having a second slide that is moveable from a first position, wherein the wash receptacle and the specimen receptacle are in open communication when the first slide is in the second position, and a second position, wherein communication between the wash receptacle and the specimen receptacle is closed. The growth chamber additionally includes a cuvette extending at least partially from the growth chamber and in open communication with the specimen receptacle when the second slide is in the second position. The system may additionally include a base unit having a cuvette receptacle for receiving the cuvette of the growth chamber, an illumination source positioned in the base unit to illuminate the cuvette when positioned in the cuvette receptacle, and at least one detector positioned in the base unit to collect data about any contents of the cuvette when positioned in the cuvette receptacle.

A thermal device may be positioned in the base unit to change the temperature of any contents of the cuvette when the cuvette is positioned in the cuvette receptacle. A wash port may be associated with the wash receptacle and adapted to allow introduction of a wash fluid into the wash receptacle from the exterior of the growth chamber. A filter may be positioned between the wash receptacle and the specimen receptacle configured to prevent the swab tip from moving from the wash receptacle to the specimen receptacle when the first slide is in the second position. A frame may surround the cuvette and define a pair of openings side opening and a bottom opening that permit access to the cuvette. A magnetic stirring assembly may be positioned in the base unit and position to drive a stirring bar positioned in the cuvette. The decapitation unit may be cylindrical and comprise an upper portion defining the swap port and a lower portion defining the swab receptacle, with the cutting instrument coupled between the upper portion and the lower portion and moveable in response to rotation of the upper portion relative to the lower portion from a non-cutting position to a cutting position that will sever the tip from any swab extending through the swab port and close the swab port. The first slide and the second slide may be unidirectional to prevent contamination or improper movement of a specimen through the system. The thermal device is configured to provide a range of temperatures that allows for growth of any biological specimens in the cuvette, for suppression of growth of any biological specimens in the cuvette, and for killing of any biological specimens in the cuvette. The detector may comprise a spectrometer or an optical imager or a combination of both types of detectors.

The system thus supports the collection, growth and analysis of biological specimens, such as Gram positive and Gram negative prokaryotic organisms that may or may not represent a threat to health. The system can support the growth of a biological specimen of unknown Gram-staining designation, determine the extent and rate of growth and replication of the biological specimen, determine whether the specimen will form a biofilm, and support delivery for subsequent serological and omni-omic analyses. Samples collected with a sterile swab are isolated using a decapitation module that can be interlocked with a culture module where the sample may be washed and stained. The culture module may then be interfaced with a base station for culturing and optical/spectral monitoring. Cell growth and replication will be monitored with an array of collimated beams of polarized laser light whose amplitudes and scatter will be monitored for the culture media (with particles) and for cylindrical rods immersed in the culture media. Estimation of the distribution of particle and film sizes may be made using forward scatter, diffraction, and bidirectional reflectance distribution of light of specific wavelengths. Culture assessment is performed with fluorescent dyes selective for dynamic markers of culture growth (e.g., DNA, metabolism, etc.), as well as molecular signatures using Raman and other optical methods. Laser light and fluorescence emissions are captured with two dimensional diode arrays whose output will provide amplitude and spatial distributions corresponding to changes in particle count, density, size distributions, and molecular composition, and simultaneously with linear diode arrays arranged with relation to a diffraction grating such that individual diodes in the linear array receive photons of specific wavelengths (e.g., an optical spectrum) of light emitted by the sample. Such emissions may be due to excitation-emissions of added dyes, and/or intrinsic excitation-emissions of samples (e.g., due to characteristic molecules, metabolism of non-fluorescent, self-quenching fluorescent substrates, etc.). The system provides for controlled mechanical stirring of the sample, and control of selectable sample growth temperature, sample growth inhibition (e.g., by cooling), and sample destruction (e.g., by heating to 120° C.). Access ports permit culture chamber sampling for extra-chamber culturing, serology, and omni-omic analyses. Chamber/device temperature, location of sample collection and growth rates are also monitored and recorded and displayed. The system may thus include onboard computing resources for control, communication and analyses of data including analyte identification through spectral and image analysis and spectral and image libraries.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
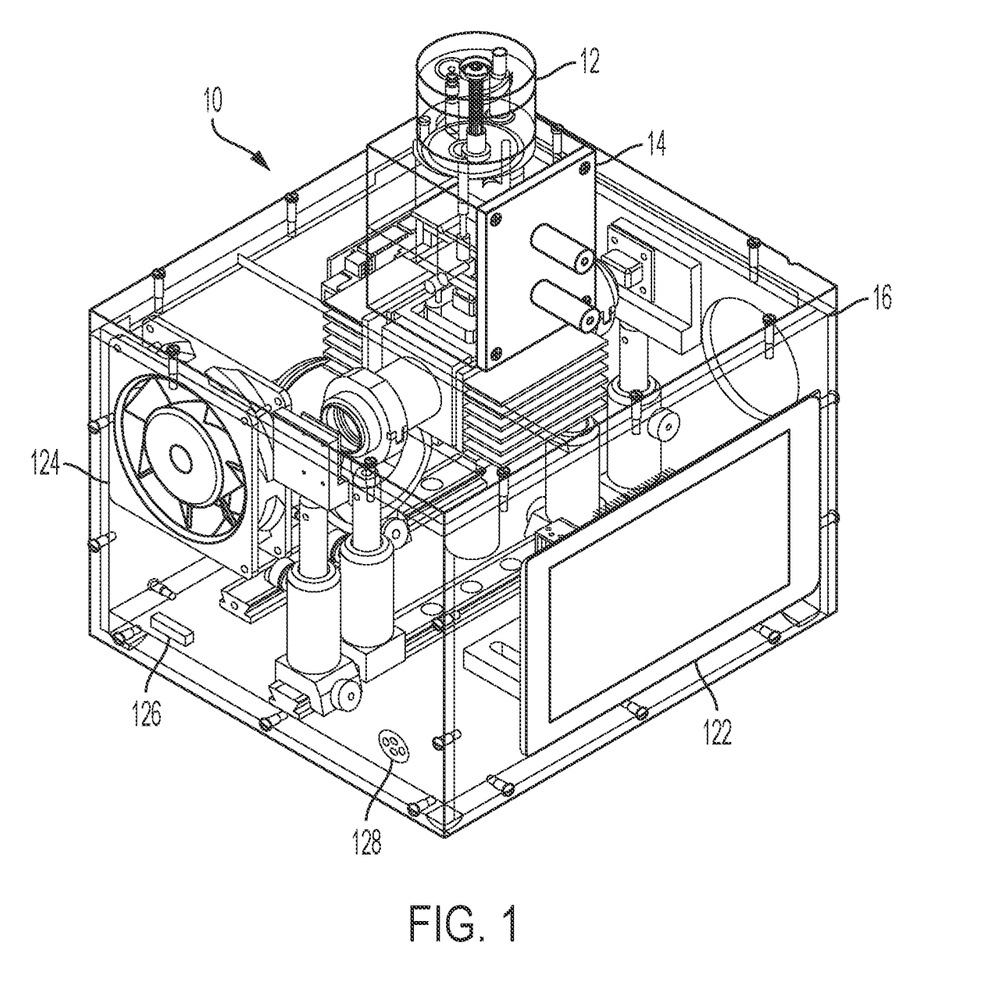
FIG. 1 is a perspective view of a liquid culture growth system according to the present invention.

Referring to the figures, wherein like numerals refer to like parts throughout, there is seen in FIG. 1 a liquid culture growth system 10 for the safe collection and expansion of biological agents and other materials. System 10 comprises a sample decapitation unit 12 that can sever and isolate the tip of a sample collector, such as a swab, after the collector is used to obtain a biological specimen. Decapitation unit 12 is coupled to a staged growth chamber 14 that can receive the severed collector tip, wash the biological specimen from the severed tip, separate the tip from the biological specimen, and supply a predetermined growth media for culturing whatever biological agents may be present in the specimen. Growth chamber 14 may be coupled to a base station 16 for application of heating or cooling to the specimen as well as optical analysis of the culturing of the specimen.

Figure 2:
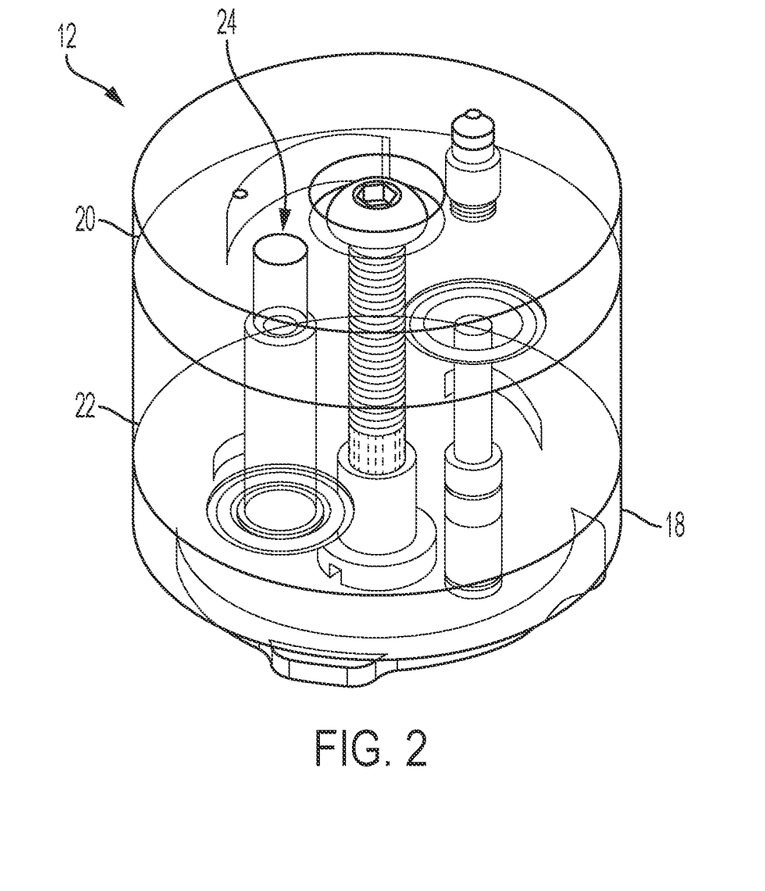
FIG. 2 is a perspective view of a decapitation unit according to the present invention.
Figure 3:
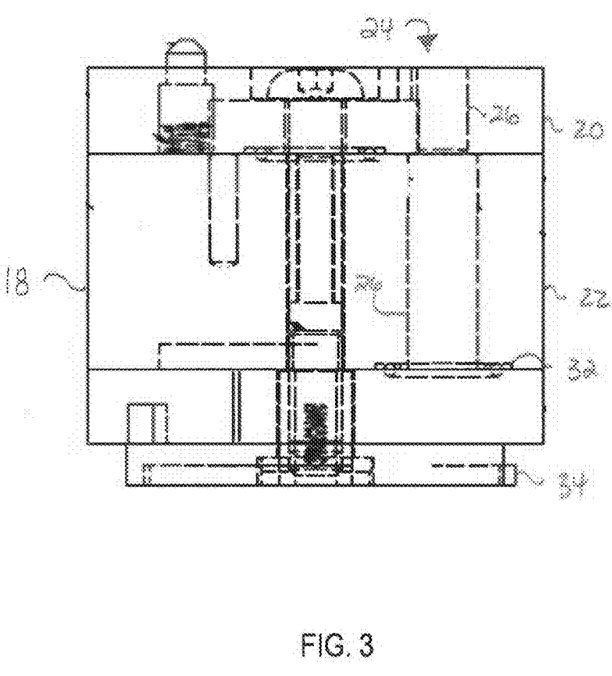
FIG. 3 is cross-sectional view of a decapitation unit according to the present invention.

Referring to FIGS. 2 and 3, decapitation unit 12 comprises a cylindrical housing 18 having an upper portion 20 that is rotatably mounted to a lower portion 22. A longitudinal port 24 extends from the exterior of housing 18 through upper portion 20 and into lower portion 22. The upper end 26 of longitudinal port 24 is in open communication with the exterior of housing 18 and is dimensioned to accept a culture swab that has been used to collect a biological specimen. Rotation of upper portion 20 relative to lower portion 22 causes a blade 28 formed in a sidewall of longitudinal port 24 at the juncture of upper portion 20 and lower portion 22 to sever the tip of the culture swab. The lower end 30 of longitudinal port 24 will thus capture any severed tip therein while allowing the remaining portion of the swab to be removed from the upper portion of longitudinal port 24. The lower end 30 of longitudinal port 24 extends through the lower portion of housing 18. A normally closed valve 32 in the end of longitudinal port 24 prevents severed tip from exiting decapitation unit 12 unless decapitation unit 12 is coupled to staged growth chamber 14. For example, interconnection of decapitation unit 12 and staged growth chamber 14 may be accomplished by a bayonet style interlock 34 formed into the bottom of housing 18 so that decapitation unit 12 may be secured to staged growth chamber 14 to reduces the chance of accidental separation and potential for contamination. When decapitation unit 12 and staged growth chamber 14 are moved in the interlocked position, valve 32 moved into the open position. Appropriately located O-rings provide for mechanical seals among components to insure absence of sample leakage or contamination. Decapitation unit 12 may include an additional port 24 and blade 28 for capturing and retaining a second swab tip to serve as a control or reference sample.

Figure 4:
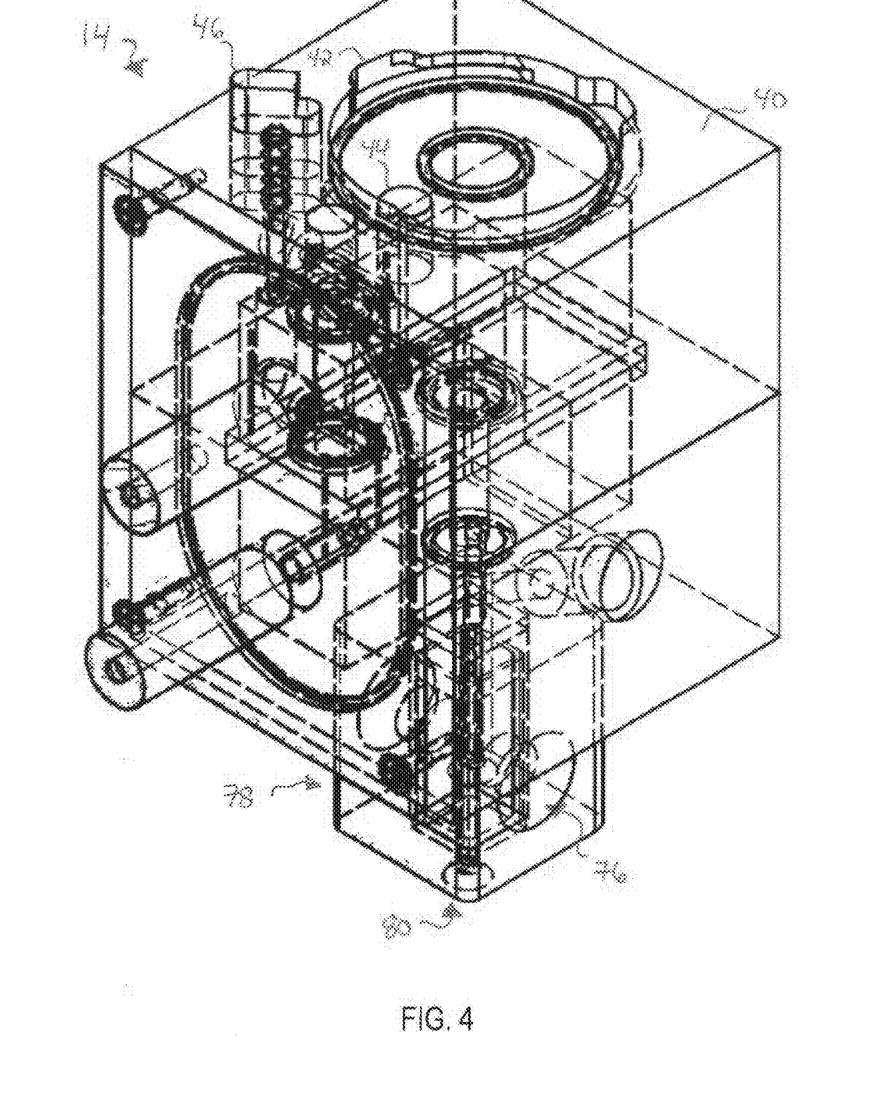
FIG. 4 is a perspective view of a growth chamber according to the present invention.
Figure 5:
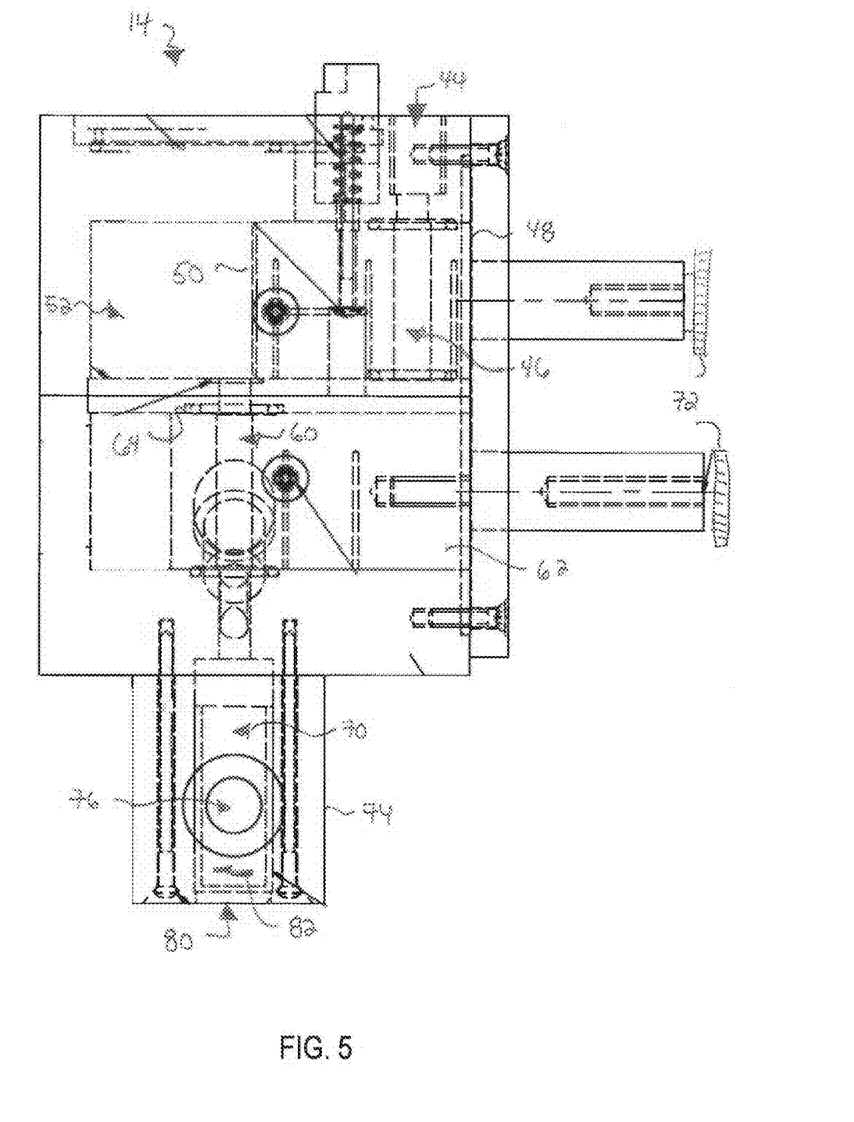
FIG. 5 is a cross-sectional view of a growth chamber according to the present invention.

Referring to FIGS. 4 and 5, staged growth chamber 14 comprises an upper surface 40 having a fitting 42 for interconnection to bayonet style interlock 34 of decapitation unit 12. Fitting 42 includes a receiving port 44 that is positioned to align with longitudinal port 24 of decapitation unit 12 when decapitation unit 12 is moved into the interlocked position therewith. A spring loaded lock 46 engages decapitation unit 12 when decapitation unit 12 is moved into the interlocked position. As valve 32 of decapitation unit 12 opens when decapitation unit 12 is interlocked with staged growth chamber 14, longitudinal port 24 will be placed into open communication with receiving port 44 of fitting 42, thereby allowing any severed swab tip in longitudinal port 24 to pass into receiving port 44. Receiving port 44 is in communication with a first receptacle 46 positioned in a first end 48 of a first slide 50 positioned in a first slide chamber 52. First slide chamber 52 additionally includes a sealed access port 54 for introducing from the exterior of staged grown chamber 14 a biological wash that can release any biological material positioned on severed tip.

Once wash has been introduced, first slide 50 is movable from a first position, where first receptacle 46 is aligned with receiving port 44 and can receipt a swab tip, to a second position where first receptacle 46 is sealed off from receiving port 44 and placed into communication with a second receptacle 60 in a second slide 62 positioned below first slide 50 in staged growth chamber 14. A filter 64 (or screen or similar mechanism to retain the swab tip) is positioned between first receptacle 46 and second receptacle 60 restricts swab tip from movement while allowing the wash liquid containing the collected biological sample to drain into second receptacle 60. Once the wash liquid has drained into second receptacle, second slide 62 may be moved to isolate second receptacle 60 from first receptacle 46 and put second receptacle 60 into communication with a cuvette 70 positioned below second slide 62 so that the wash liquid may drain therein. Once the wash liquid has flowed into cuvette 70, cuvette 70 may be isolated by movement of second slide 62. Second slide 62 may comprise a longitudinal slide body such as that seen in FIG. 5, or a rotating slide body having a port formed there through for selectively providing communication between first slide chamber and cuvette based on the rotational alignment of the port. First slide 50 and second slide 62 may be provided with knurled handles 72 to improve handling when a user is wearing gloves, such as when system 10 is positioned inside a biological grade glove box. First slide 50 and second slide 62 may include ball-stop detents to assist with the positioning of the sides in the appropriate locations. First slide 50 and second slide 62 are also preferably one-directional to prevent cross-contamination or the release of any sample once captured inside system 10. As seen in FIG. 5, staged growth chamber 14 includes a frame 74 positioned about cuvette 70 and including a pair of opposing lateral openings 76 and 78, and an open bottom 80. Cuvette 70 is preferably pre-loaded with a magnetic stirring bead 82.

Figure 6:
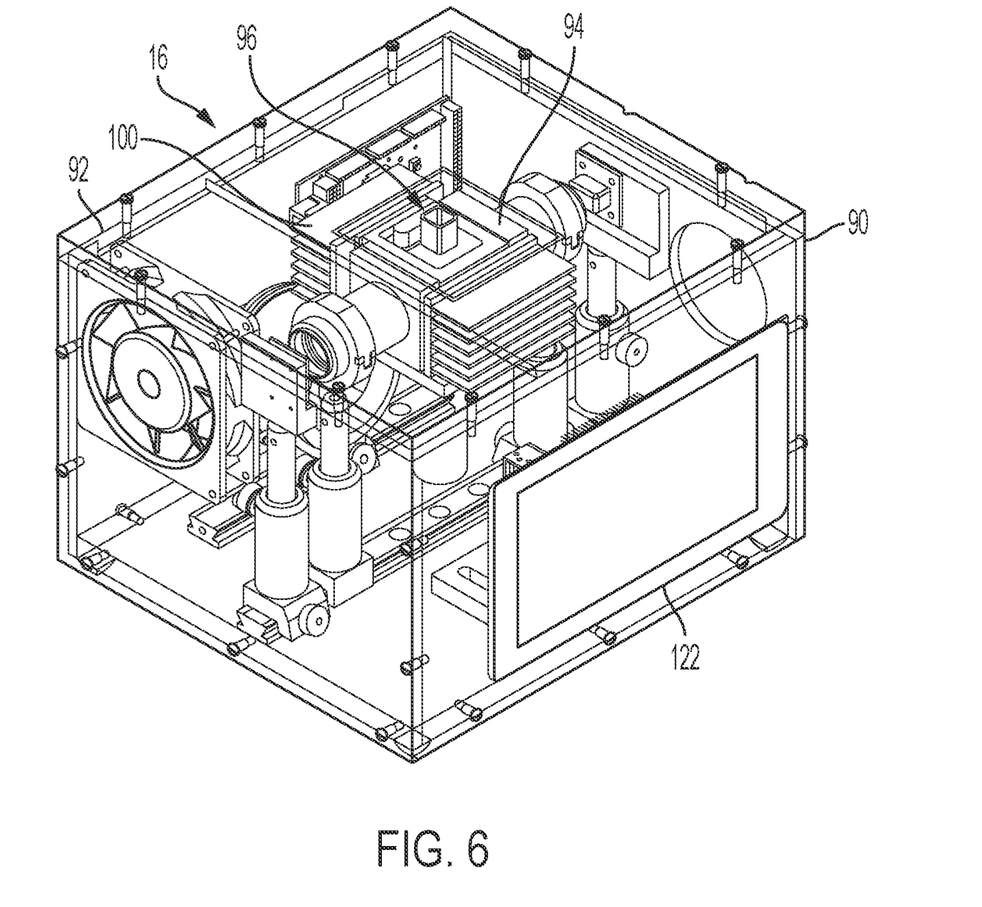
FIG. 6 is a perspective view of a base station according to the present invention.
Figure 8:
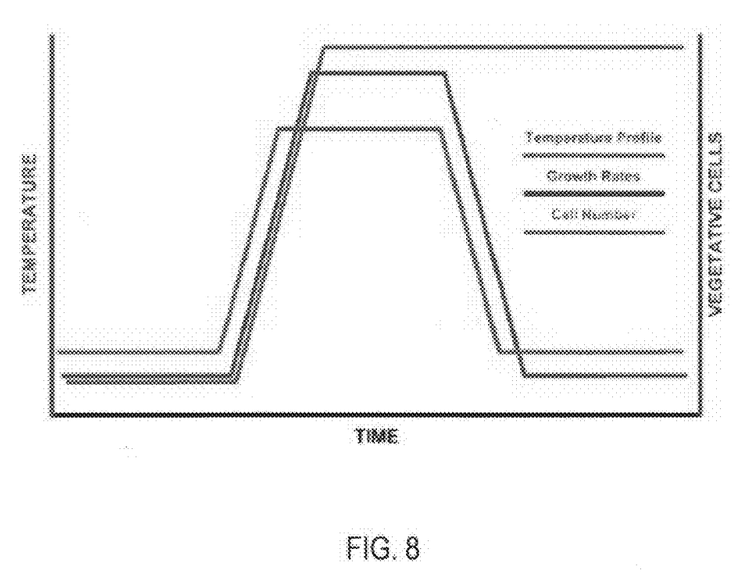
FIG. 8 is a chart of biological sample handling using liquid culture growth system according to the present invention.
Figure 9:
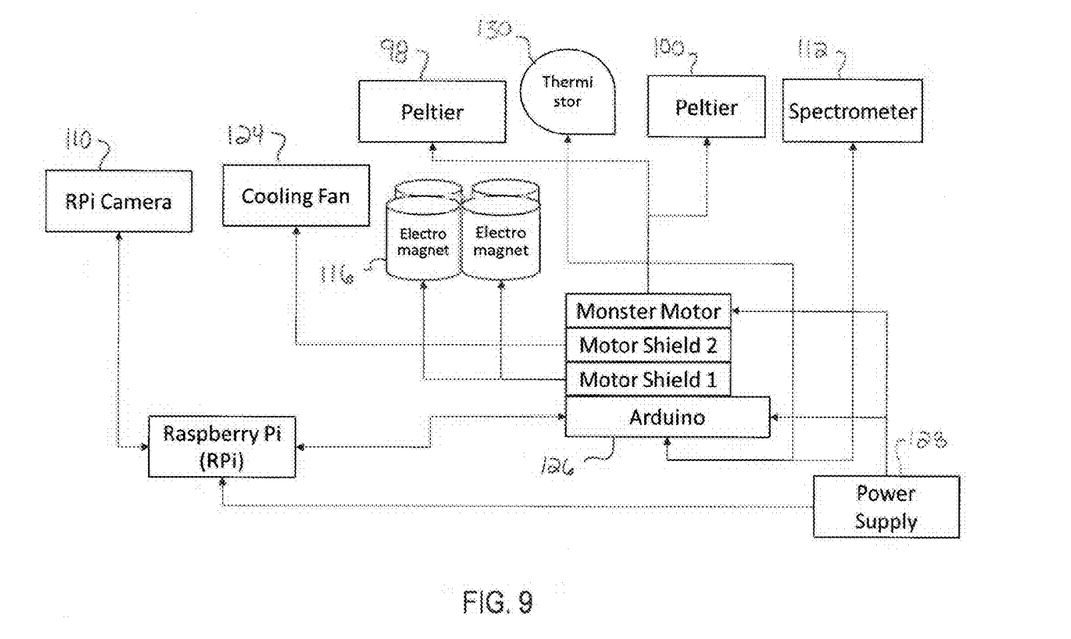
FIG. 9 is a schematic of the electrical components of the system according to the present invention.

Referring to FIGS. 6 and 9, base station 16 comprises a housing 90 having a planar upper surface 92 that includes a receptacle 94 having an opening 96 dimensioned to accept frame 74 and cuvette 70 therein when staged growth chamber 14 is positioned on base station 16. Receptacle 94 and frame 74 include corresponding geometric keying so that receptacle 94 will only accept frame 74 therein when the two parts are positioned in a predetermined orientation relative to each other. Receptacle 94 further includes a pair of heating/cooling elements 98 and 100, such as Peltier devices, positioned on either side of receptacle 94 to provide temperature control via thermoelectric heat transfer and thermistor 130 to monitor temperature, such as that seen in FIG. 8. When receptacle 94 and frame 74 are properly keyed, heating/cooling elements 98 and 100 are positioned proximately to the opposing sides of frame 74 that do not include opposing lateral openings 76 and 78. The thermoelectric temperature regulation of cuvette 70 with heating/cooling elements 98 and 100 allows for growth at preferred temperatures of 20° C. (298° K) to 37° C. (310° K), suppression of growth at temperatures of 2° C. (275° K), and killing of cultures at 120° C. (393° K), but it should be recognized that other temperatures are attainable and may be employed.

Figure 7:
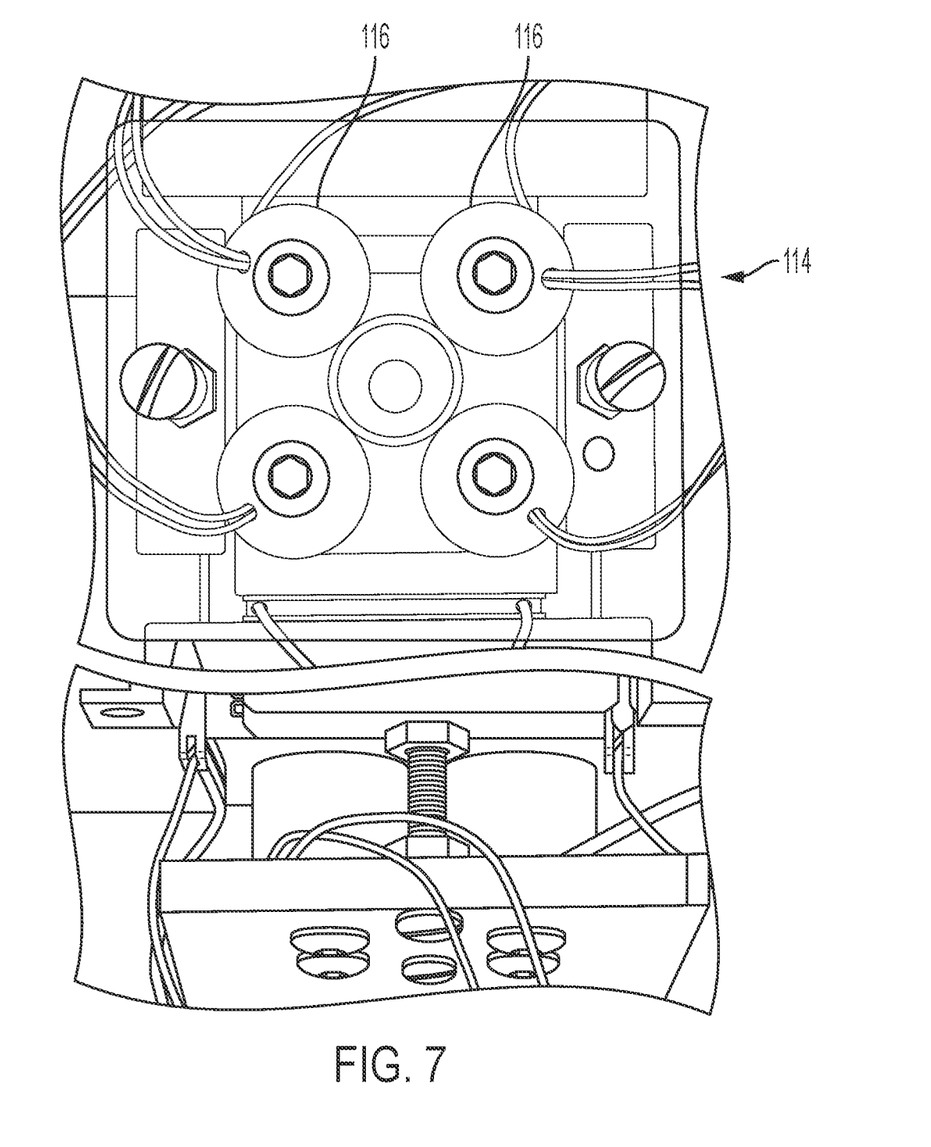
FIG. 7 is a perspective view of a magnetic stirring assembly base station according to the present invention.

Receptacle 94 further includes a pair of detectors 110 and 112 positioned on opposing sides of frame 74 when inserted therein. Due to keying of receptacle 94 and frame 74, detectors 110 and 112 will align with opposing lateral openings 76 and 78 in frame, thus enabling detectors to take measurements of cuvette 70. Detectors 110 and 112 may comprise a diode array spectrometer and an RGB backlit CMOS image sensor for direct simultaneous evaluation of the contents of cuvette, such as amplitude and spatial distributions corresponding to changes in particle count, density, size distributions, and molecular composition. As an example, inclusion of the intercalating DNA-selective dye H33342 can permit direct assessment of DNA synthesis and accumulation in the culture chamber, i.e., a direct assessment of prokaryotic cell replication. Similarly, other dyes may be used to assess the level of DNA present due to dead cells (e.g., propidium iodide) and cellular metabolism (e.g., resulting in production of nitric oxide (NO)) (e.g., DAF-FM Diacetate (4-Amino-5-Methylamino-2',7'-Difluorofluorescein Diacetate). Whose excitation and emission spectra are (a) known) and (b) distinguishable using spectral resolution and numerical deconvolution methods known in the art. Base station 16 further includes a magnetic stirring assembly 114 positioned below receptacle 94. As seen in FIG. 7, magnetic stirring assembly 114 preferably comprises four electromagnets 116 positioned equidistantly about and below receptacle 94 to drive magnetic stirring bead 82 in both a stirring motion, and to apply magnetic forces unequally so that bead 82 is pulled to one side of cuvette 70 when stirring is complete to allow for unencumbered illumination of cuvette 70 from below and imaging of the contents of cuvette 70 by detectors 110 and 112.

A light source 120 is positioned directly below receptacle 94 and aligned to provide illumination upwardly into the bottom of cuvette 70. Light source 120 is preferably a bank of four LED lasers that can provide a variety of single wavelength illumination for different imaging applications and biological stain options used in analytical light and spectral microscopy. Light from those LEDs is conveyed via liquid light guide or other means to a port on the Base Unit, which collimates the light, and conveys it to a parabolic reflector located under the specimen chamber, and light reflected by the parabolic reflector is projected to an aperture of the specimen receiver to be conveyed into the sample cuvette and thus be available for illumination of the sample wash and excitation of fluorescent molecules, scattering by sample particulates, and ultimate capture by the detectors. Alternatively, the LEDs may be integrated into base station 16 for direction application of illumination. Referring to FIG. 9, base station 16 may further include a human interface 122, such as a display screen and keyboard input, powered ventilation 124 to assist with rapid heating or cooling of cuvette 70, control electronics packages 126 for driving the various components such as magnetic stirring assembly 114, illumination source 120, and heating/cooling elements 98 and 100. Base station 16 may further include a power port 128 having a large ring connector for coupling base station 16 to an exterior power source while a user is wearing gloves. It should be recognized that base station 16 could be provided with an internal power source such as a battery assembly. Chamber/device temperature may also be monitored and recorded and GPS signals used to track the location of base station 16. Base station 16 may further include memory for recording and storing data locally (e.g., microSDHC/microSDXC UHS-I memory cards) and the appropriate wireless (e.g., Bluetooth) or wired transmission (e.g., USB) chip packages for communicating stored data to external host devices. Control electronics packages 126 is programmed to drive the various elements of base station 16 to culture any sample, monitor growth, halt culturing at a predetermined time or amount of growth, and optionally destroy any culture if necessary. Temperature feedback control allows control electronics packages 126 to sense local collection temperatures and control cultures with programmed drops to reduce growth-rate when appropriate. System 10 may be used inside a field glove box to ensure the safety of forward operators while allowing for rapid detection and identification of threats. Human interface 122 can display the progress of operations of base stations 10, which are preferably automated, report the results of operations, and allow for user input. System 10 may provide for communication with an operator or analyst via touch screen display, USB, Wi-Fi, Bluetooth, Ethernet or other current or future means of electronic or optical communications as is known in the art. System 10 may optionally include micro- or nano-fluidic coupling interfaces for providing some or all of the culture to external analysis system, such as polymerase chain reaction (PCR) and related DNA sequencing analysis systems.

The present invention thus provides a means for collection and support of environmental samples, including growth and analysis of Gram-positive and Gram-negative prokaryotic organisms, fungal specimens, etc. that may or may not represent a threat to human and non-human health, in a safe manner and with the ability for ready decontamination and disposal of the various elements. System 10 can provide for the collection, growth and analysis of an unknown biological sample, while preventing cross-contamination of the sample and exposure of personnel to organisms in culture and while harvesting the sample. System 10 may also integrate with up-stream and down-stream analytics (e.g., transcriptomics, metabolomics, etc.), is amenable to large-scale manufacturing and distribution; and is operable by non-technical personnel in-theater (including users in Level A personal protective suits). More specifically, system 10 can (1) support the growth of a bacterial isolate of unknown Gram-staining designation or population spectrum and support aerobic or anaerobic growth; (2) provide non-destructive determination of the extent and rate of growth and replication of the isolate population; (3) determine if members of the isolate culture will form a biofilm; (4) support subsequent serological and omni-omic analyses of the sample; and (5) safely and successfully kill contained organisms if necessary.

As described above, the present invention may be a system, a method, and/or a computer program associated therewith and is described herein with reference to flowcharts and block diagrams of methods and systems. The flowchart and block diagrams illustrate the architecture, functionality, and operation of possible implementations of systems, methods, and computer programs of the present invention. It should be understood that each block of the flowcharts and block diagrams can be implemented by computer readable program instructions in software, firmware, or dedicated analog or digital circuits. These computer readable program instructions may be implemented on the processor of a general purpose computer, a special purpose computer, or other programmable data processing apparatus to produce a machine that implements a part or all of any of the blocks in the flowcharts and block diagrams. Each block in the flowchart or block diagrams may represent a module, segment, or portion of instructions, which comprises one or more executable instructions for implementing the specified logical functions. It should also be noted that each block of the block diagrams and flowchart illustrations, or combinations of blocks in the block diagrams and flowcharts, can be implemented by special purpose hardware-based systems that perform the specified functions or acts or carry out combinations of special purpose hardware and computer instructions.

What is claimed is:

1. A specimen collection system, comprising:
    a swab decapitation unit having a swab port dimensioned to accept a sample swab, a cutting instrument positioned at an end of the swab port and moveable to sever a tip of the swab, a swab receptacle for retaining the severed tip of the swab, and a valve controlled by a first interlock in communication with the receptacle;
    a growth chamber having an entry port with a second interlock that is adapted to be coupled to the first interlock and to open the valve of the decapitation unit so that the entry port is in communication with the swab receptacle when the first interlock and second interlock are coupled together; and
    a wash receptacle positioned in the growth chamber in communication with the entry port and having a first slide that is moveable between a first position, wherein the entry port and the wash receptacle are in open communication, and a second position, wherein the entry port and the wash receptacle are isolated from each other;
    a specimen receptacle coupled to the wash receptacle and having a second slide that is moveable from a first position, wherein the wash receptacle and the specimen receptacle are in open communication when the first slide is in the second position, and a second position, wherein communication between the wash receptacle and the specimen receptacle is closed; and
    a cuvette extending from the growth chamber and in open communication with the specimen receptacle when the second slide is in the second position.

2. The specimen collection system of claim 1, further comprising:
    a base unit having a cuvette receptacle for receiving the cuvette of the growth chamber;
    an illumination source positioned in the base unit to illuminate the cuvette when positioned in the cuvette receptacle;
    at least one detector positioned in the base unit to collect data about any contents of the cuvette when positioned in the cuvette receptacle; and
    a thermal device positioned in the base unit to change the temperature of any contents of the cuvette when positioned in the cuvette receptacle.

3. The specimen collection system of claim 2, further comprising a wash port associated with the wash receptacle and adapted to allow introduction of a wash fluid into the wash receptacle from the exterior of the growth chamber.

4. The specimen collection system of claim 3, further comprising a filter positioned between the wash receptacle and the specimen receptacle configured to prevent the swab tip from moving from the wash receptacle to the specimen receptacle when the first slide is in the second position.

5. The specimen collection system of claim 4, further comprising a frame that surrounds the cuvette and defines a pair of openings side opening and a bottom opening that permit access to the cuvette.

6. The specimen collection system of claim 5, further comprising a magnetic stirring assembly positioned in the base unit and position to drive a stirring bar positioned in the cuvette.

7. The specimen collection system of claim 6, wherein the decapitation unit is cylindrical and comprises an upper portion defining the swap port and a lower portion defining the swab receptacle.

8. The specimen collection system of claim 7, wherein the cutting instrument is coupled between the upper portion and the lower portion and moveable in response to rotation of the upper portion relative to the lower portion from a non-cutting position to a cutting position that will sever the tip from any swab extending through the swab port and close the swab port.

9. The specimen collection system of claim 8, wherein the first slide and the second slide are unidirectional.

10. The specimen collection system of claim 9, wherein the thermal device is configured to provide a range of temperatures that allows for growth of any biological specimens in the cuvette.

11. The specimen collection system of claim 10, wherein the thermal device is configured to provide a range of temperatures that allow for suppression of growth of any biological specimens in the cuvette.

12. The specimen collection system of claim 11, wherein the thermal device is configured to provide a range of temperatures that allow for killing of any biological specimens in the cuvette.

13. The specimen collection system of claim 12, wherein the detector comprises a spectrometer.

14. The specimen collection system of claim 12, wherein the detector comprises an optical imager.

* * * * *